Figure 1:
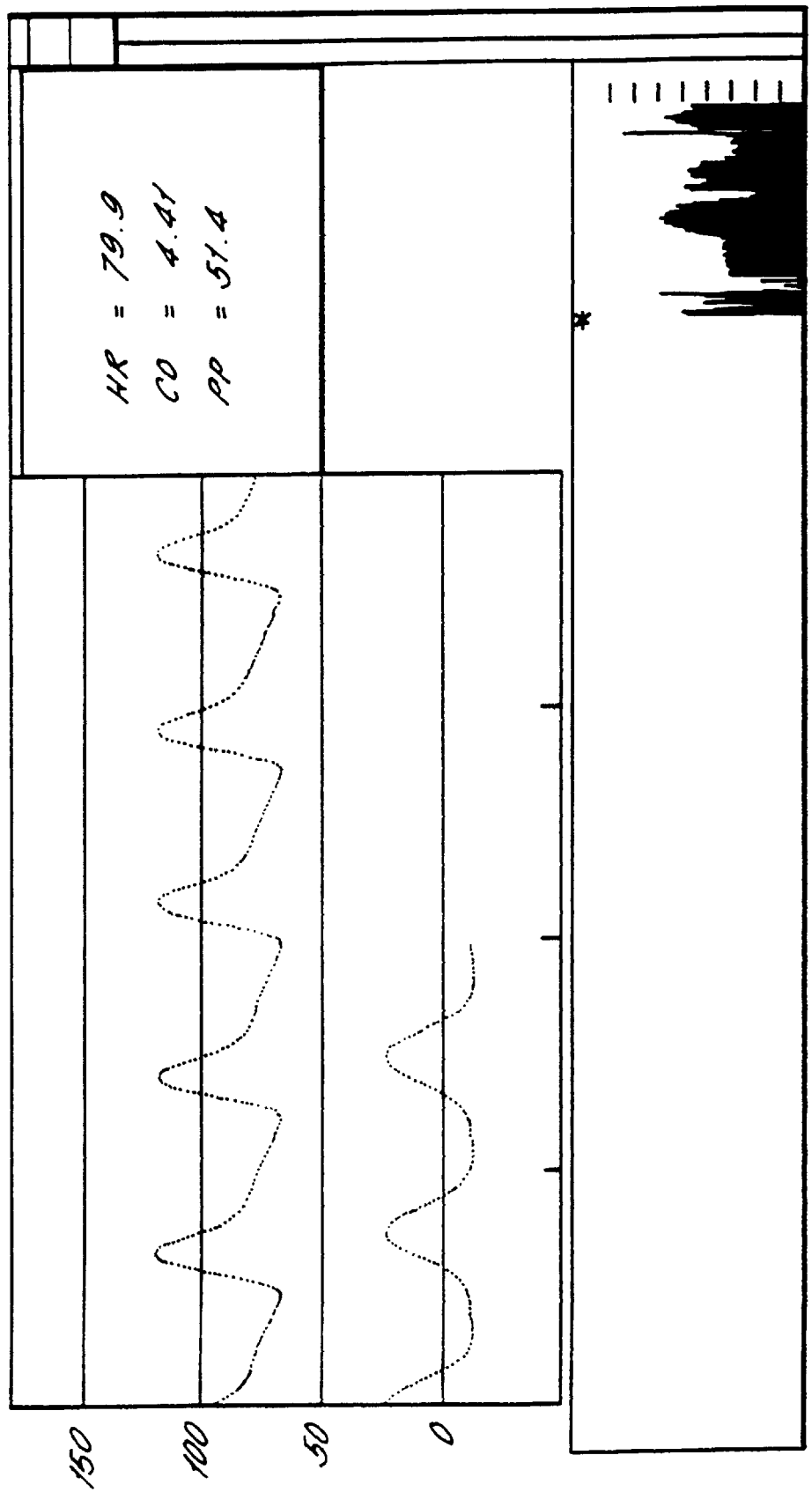

United States Patent [19]
Band et al.

[11] Patent Number: 6,071,244
[45] Date of Patent: Jun. 6, 2000

[54] METHOD AND APPARATUS FOR THE MEASUREMENT OF CARDIAC OUTPUT

[75] Inventors: David Marston Band, Surrey; Nicholas William Fox Linton; Robert Antony Fox Linton, both of London; Terence Kevin O'Brien, Great Shelford, all of United Kingdom

[73] Assignee: Monitoring Technology Limited, London, United Kingdom

[21] Appl. No.: 09/101,420

[22] PCT Filed: Jan. 3, 1997

[86] PCT No.: PCT/GB97/00017

§ 371 Date: Apr. 15, 1999

§ 102(e) Date: Apr. 15, 1999

[87] PCT Pub. No.: WO97/24982

PCT Pub. Date: Jul. 17, 1997

[30] Foreign Application Priority Data

Jan. 5, 1996 [GB] United Kingdom .................... 9600209

[51] Int. Cl.[7] .................................................. A61B 5/029
[52] U.S. Cl. ........................................................... 600/526
[58] Field of Search ................................................ 600/526

[56] References Cited

PUBLICATIONS

Erlanger, et al., An Experimental Study of Blood–Pressure and of Pulse–Pressure in Man, Johns Hopkins Hospital Reports 12: 145–378 (1904).

Jansen et al., Continuous Cardiac Output Monitoring by Pulse Contour During Cardiac Surgery, European Heart Journal, 11: (1990) 27–33 (1990).

Irlbeck, et al., Die kontinuierliche Messung des Herzzeitvolumens mit der Pulskonturanalyse, Anaesthesist 44: 493–500 (1995) (English abstract on p. 494).

W. F. Hamilton, Ph.D., The Lewis A. Connor Memorial Lecture—The Physiology of the Cardiac Output, Hamilton, Circulation, VII: 527–543 (1953).

*Primary Examiner*—William E. Kamm
*Attorney, Agent, or Firm*—Bacon & Thomas

[57] ABSTRACT

A method for the measurement of cardiac output in a patient in which the arterial blood pressure waveform of a patient from a blood pressure monitoring device over a period of time is subjected to various transformations and corrections, including autocorrelation, whereby the pulsatility and heart rate of the patient are obtained. The nominal stroke volume is then calculated from the pulsatility and the nominal caridac output obtained by multiplying the stroke volume by the heart rate.

17 Claims, 5 Drawing Sheets

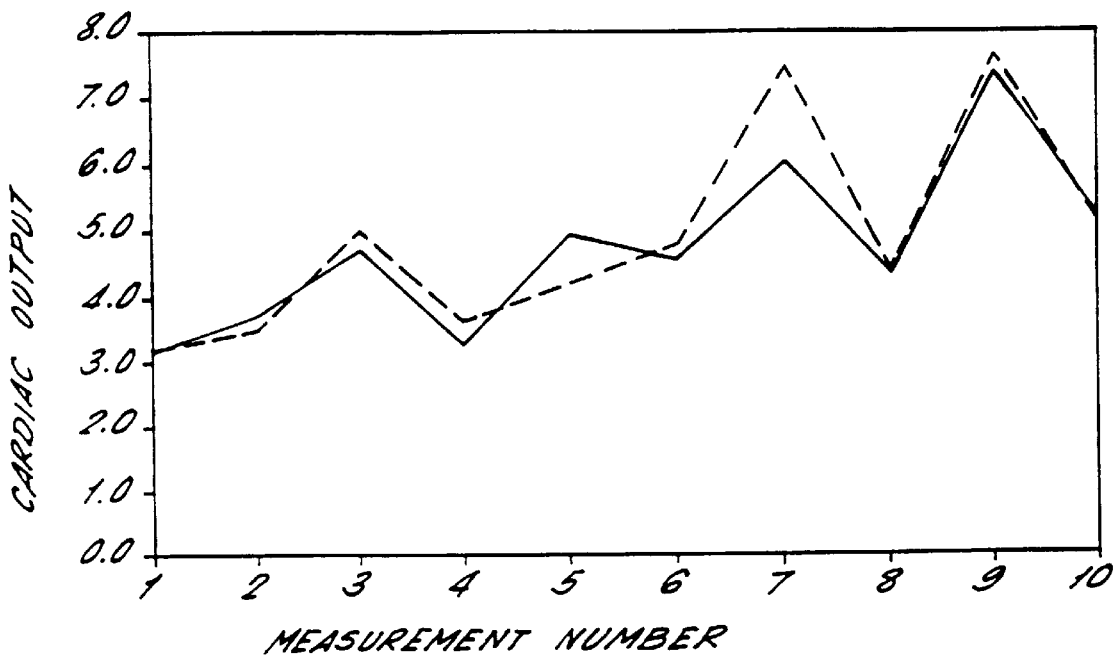
FIG. 5a. PATIENT 1.   ----- PRIOR ART   ——— INVENTION
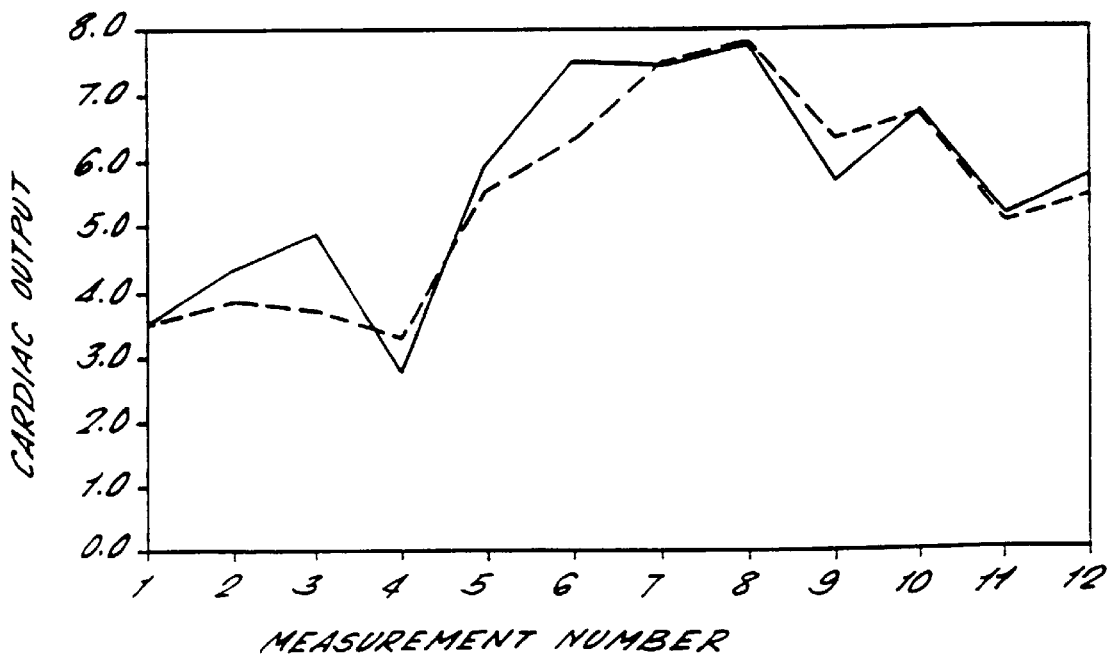
FIG. 5b. PATIENT 2.   ----- PRIOR ART   ——— INVENTION

METHOD AND APPARATUS FOR THE MEASUREMENT OF CARDIAC OUTPUT

The present application is the U.S. national phase of international application number PCT/GB97/00017.

The present invention relates to an improved method and apparatus for the measurement of cardiac output and in particular to an improved method and apparatus which has a rapid rate of response.

It has been suggested since at least 1904 (Erlanger and Hooker, Bull. John Hopkins Hosp. 15:179) that the arterial pulse pressure could be regarded as a rough index to the stroke volume of the heart and, in combination with the heart rate, could provide the cardiac output. This approach was found to be simplistic, particularly at high arterial pressures where the relationship breaks down.

Accordingly, various correction factors were introduced such as age, weight, height and aortic compliance/distensibility. Whilst these correction factors improved the results there was still a disturbing number of conditions in patients where disappointing results were obtained, e.g. patients with low cardiac outputs and high arterial pulse pressures, or vice versa.

Various approaches to the derivation of cardiac output from pressure waveform analysis have also been attempted: e.g. from the pulse wave velocity and by integration of the pulse contour. As stand alone methods these have proved equally disappointing with a major difficulty in measuring the major morphological features of the waveform in pathologic situations, e.g. peaks, systolic areas, dicrotic notch etc. During major surgery, or in an intensive care situation, the pressure waveform may not exhibit a dicrotic notch at all.

In addition to using correction factors Hamilton (The physiology of cardiac output. Circulation 8: 527, 1953) suggested that cardiac output could be derived from a patient's blood pressure pulse height following calibration by another cardiac output method, such as dye dilution. Furthermore, more recently Jansen et al (Continuous cardiac output monitoring by pulse contour during cardiac surgery, Eur. Heart Journal 1990, 11:26–32) discuss a 'corrected pulse contour' method where the pulse contour is calibrated used a thermodilution technique.

U.S. Pat. No. 5,400,793 describes a method for determining blood stroke volume from a pulsatile aorta bloodflow pressure signal in a subject. The method uses a simulation model of the aorta as a transmission line supplemented with a Windkessel compliance including a pressure volume relationship for the aorta that is known in the art.

In essence, the pressure waves recorded from the aorta are used to calculate the characteristic impedance of the transmission line, and the parameters of the Windkessel are adapted until the pressure in the model is consistent with that recorded in the aorta. The flow indicated by the model is then integrated over the period of systole. Ideally, this method requires a high fidelity pressure recording system in the aorta. Although a method of correcting a pressure measurement in a peripheral artery is mentioned, this method cannot be used with the poor frequency response given by most pressure transducers that are now routinely in clinical use: in the presence of noise an "anti-resonance filter" cannot recover the information that is lost by the poor quality of these transducers.

U.S. Pat. No. 5,390,679 discloses a method of determining cardiac output from a cardiac pressure waveform in which the pressure waveform is continuously sensed and converted into a digital data stream. When a complete beat frame of data is sensed, the processor extracts a plurality of features from the sensed waveform which characterises the waveform. This data is compared with stored representative pressure waveforms (RPW's) which have a known cardiac output obtained by applying a pattern recognition technology thereto. It is necessary, however, to store thousands of RPW's in order to build up a data base against which the cardiac pressure waveform can be compared.

Finally, Irlbeck et al (Continuous measurement of cardiac output with pulse contour analysis, Anaesthetist 1995, 44:493–500) propose that the calculation of stroke volume and cardiac output is possible by analysing the area under the systolic part of the arterial pulse pressure waveform, together with an individual calibration factor (Zao) to account for individually variable vascular impedance.

Unfortunately, this analysis is of limited applicability to clinical measurement since the waveforms recorded for the patients for whom it would be really useful often do not show the features required for the recognition of the systolic part of the pressure waveform. The pulse is often irregular and each heartbeat may generate several minor waves superimposed upon the primary pulse waveform.

We have now developed an improved method and apparatus for measuring cardiac output which does not suffer the aforementioned disadvantages of the prior art methods discussed above.

Accordingly, in a first aspect the present invention provides a method for the measurement of cardiac output in a patient, which method comprises the steps of:

(i) recording and storing the arterial blood pressure waveform of a patient from a blood pressure monitoring device over a period of time;

(ii) subjecting the waveform obtained in step (i) to a non-linear transformation that corrects for the variation of the characteristics of the arterial system with pressure;

(iii) subjecting the corrected waveform curve from step (ii) to autocorrelation in order to derive the pulsatility and heart rate of the corrected waveform;

(iv) calculating the nominal stroke volume from the pulsatility; and (v) obtaining the nominal cardiac output by multiplying the nominal stroke volume by the heart rate.

In a second aspect the present invention provides a method for the measurement of cardiac output in a patient, which method comprises the steps of:

(a) recording and storing the arterial blood pressure waveform of a patient from a blood pressure monitoring device over a period of time;

(b) means for subtracting from the blood pressure waveform the mean of said blood pressure waveform and subjecting the data to autocorrelation;

(c) transforming the data from step (b) into data which relates to the pulsatility and heart rate of the waveform;

(d) calculating the nominal stroke volume from the pulsatility; and (e) obtaining the nominal cardiac output by multiplying the nominal stroke volume by the heart rate.

In carrying out either of the methods of the present invention the arterial blood pressure of a patient is monitored continuously by conventional means via an arterial line and pressure transducer, for example using a Hewlett Packard blood pressure monitoring machine. The output data from the machine is amplified and smoothed to provide a continuous blood pressure waveform. The continuous blood pressure waveform is monitored over a period of time, for example at least two patient heartbeats and generally for a period of ten seconds or less, preferably for a period of up to four seconds.

In carrying out the first method of the present invention the pressure is subjected to a non-linear transformation before the autocorrelation step whereas in other methods correction factors are generally applied at the end of the calculations.

As mentioned above, the pressure waveform obtained in step (i) of the first method is transformed, preferably via a 'look up' curve, with the mean of the data then being found and subtracted, into data which represents the pressure/volume relationship of the arterial system. The basic approximation to a look up table is known in the art and the relationship is non-linear, a series of such curves being described in Remington et al, 1948, Am. J. Physiol 153: 298–308: Volume elasticity characteristics of the human aorta and prediction of the stroke volume from the pressure pulse.

The corrected waveform from step (ii) is then subjected to autocorrelation in order to determine the pulsatility and heart rate of the transformed waveform. Autocorrelation is defined in Dictionary of Science and Technology, Academic Press, 1992, p 186.

Autocorrelation is performed by a process of multiplication and summation. Firstly, the mean of the series is found and subtracted from each of the values so that the series represents the signal moving positive and negative around a mean of zero.

Tau ($\tau$) is used to denote a time shift so that at Tau=0 each of the values of y is multiplied by itself and all of the products added together. When Tau=1 the first value is multiplied by the second, the second by the third, and so on down the series representing the record. The values obtained for each Tau are then divided by the number of points used in the correlation (say n/2) and the correlation function plotted as a function of Tau.

When Tau=0 the function has a maximum value since each of the values is being squared and the negative values become positive. If the original series represented white noise, any non-concurrent points would have a random relationship and be as likely to be positive as negative. When Tau is greater than zero the sum of the products would therefore be close to zero. However, if there is any systematic waveform contained in the original series then at an appropriate value for Tau, like is again being multiplied by like, and the autocorrelation rises to a peak.

This form of correlation is very powerful in detecting periodicities; the Tau value of the first correlation peak represents the wavelength of the periodicity. Depending upon the number of cycles sampled by the original series, further peaks may be seen representing the Tau shift at which the first waveform is being multiplied by the next but one, and so on. Therefore the interval for one heart beat can be found using autocorrelation—it is equal to the smallest value of Tau that gives a peak in the autocorrelation which is comparable to the mean square value at Tau=0.

The value of the function of Tau=0 is the mean square of the original record. Thus if the original trace were a series of cycles of a sine wave, the autocorrelation would resemble a cosine waveform, the peak values of which would be the mean square of the original sine wave. Taking the square root of the peak value gives the root mean square of the original sine wave.

The autocorrelation (of the transformed data with the mean subtracted) is also used to find the pulsatility. We define pulsatility as $$\text{pulsatility} = \sqrt{R(0)} + \sqrt{-R(\tau_{min})}$$

where $R(\tau)$ is the autocorrelation function and $\tau_{min}$ is the value of $\tau$ at which the autocorrelation is at a minimum.

Nominal stroke volume is then found by multiplying the pulsatility by a constant. The nominal cardiac output is obtained by multiplying the nominal stroke volume by the heart rate. It will be understood that the nominal stroke volume and the nominal cardiac output are uncalibrated and may be converted into calibrated data, if desired.

The stroke volume is calculated in step (iv) of the method, generally by multiplying the pulsatility by a calibration factor obtained for a particular patient using a known accurate calibration method, for example using an indicator dilution method or thermodilution method. An indicator dilution method is described, for example, in WO93/09427. The method as described in WO93/09427 is highly repeatable and only one single point calibration is required to give the cardiac output. It will be understood, however, that the method of the present invention may be used without calibration in order to show trends in or directions of change of the cardiac output of a patient.

Once the adjustment/calibration has been made then the cardiac output can be obtained by multiplying the stroke volume by the heart rate. The cardiac output can be provided as an appropriate value of few seconds coverage and as data, thereby giving a close to realtime analysis of rapidly changing events. For example, the method of the present invention can be used to monitor the cardiac output change following the administration of fluids, or to set a temporary pacemaker to an optimal rate, or to determine when administration of a vasoactive drug may be required.

Another method of adjusting/calibrating the pulsatility is by the thermodilution method but this method is not preferred since it requires multiple readings viz the averaging of at least three points in order to give a single stroke volume from which the cardiac output can be calculated and presents a significant risk to the patient.

In carrying out the second method of the present invention steps (a), (d) and (e) correspond generally to steps (i), (iv) and (v) of the first method as discussed above. Following step (a), the mean of the waveform is subtracted and the data so obtained is then subjected to autocorrelation in the manner as discussed above. The autocorrelated data then transforms into data which relates to the pulsatility and heart rate of the waveform. The calculation of the pulsatility using this method will require scaling according to the mean blood pressure, the scaling factor being equal to the slope of the pressure-volume relationship at the mean pressure.

Although the methods of the present invention have been described above generally assuring that a plurality of heart beats will be measured, it is possible to process single heart beats if they can be identified separately. Methods for identifying single heart beats are known in the art. In order to find the stroke volume of a single beat the method would be essentially the same as that described above, but to carry out the autocorrelation it would be assumed that the blood pressure repeated itself after the end of the beat.

In a further aspect the present invention provides a first apparatus for the measurement of cardiac output in a patient, which comprises:

means for monitoring the arterial blood pressure of a patient;

means for monitoring the heart rate of a patient;

means for recording and storing the arterial blood pressure waveform of a patient;

means for transforming the pressure waveform to correct for the variation of the arterial system with pressure;

means for autocorrelating the transformed data and deriving the pulsatility and heart rate of the waveform therefrom; and means to calculate the nominal cardiac output from the measurements of heart rate of the patient and the pulsatility of the waveform.

In the apparatus of the invention the means for transforming the pressure waveform preferably comprises a look up table as described above. The apparatus may also include means to calibrate the device, for example using the indicator dilution methods as discussed above.

In a still further aspect the present invention provides a second apparatus for the measurement of cardiac output in a patient, which comprises:

means for monitoring the heart rate of a patient;

means for recording and storing the arterial blood pressure waveform of a patient;

means for subtracting from the blood pressure waveform the mean of said blood pressure waveform and subjecting the data to autocorrelation;

means for transforming the autocorrelated data into data relating to the pulsatility and heart rate of the waveform; and means to calculate the nominal cardiac output from the measurements of heart rate of the patient and the pulsatility of the waveform.

Apparatus for carrying out the present invention may comprise any suitably programmed computer such as an IBM compatible computer or a Macintosh personal computer. For the analysis of indicator dilution curves, the apparatus for measuring cardiac output will include a blood sensor such as that disclosed in WO93/09427. The output of the sensor must then be digitized by an analogue-to-digital converter and input into the computer. For any other form of signals representing physical parameters, similarly, the output of some sort of transducer must be digitized to provide signals for analysis by the software loaded in a computer.

The computer program running on the computer may either display the results or can output this to some other device.

The present invention will be further described with reference to the accompanying drawings in which:

FIGS. 1 to 4 show the results obtained using method and apparatus of the present invention to analyse the arterial blood pressure recordings from four patients; and FIGS. 5a and 5b compare the cardiac output of two patients measured using the method and apparatus of the present invention compared to the prior art method as disclosed in WO 93/09427.

Referring to the drawings, in each of FIGS. 1 to 4 the top left window shows four seconds of arterial blood pressure recorded from a patient as the upper trace and below this the autocorrelation. In the upper right window the heart rate (HR), cardiac output (CO) and "pulsatility" (PP) are displayed. The bottom window shows a right to left scrolling record of previous history of the cardiac output.

FIG. 1—The arterial wave form is smooth and regular. The heart rate is 79.9 beats per minute.

Figure 2:
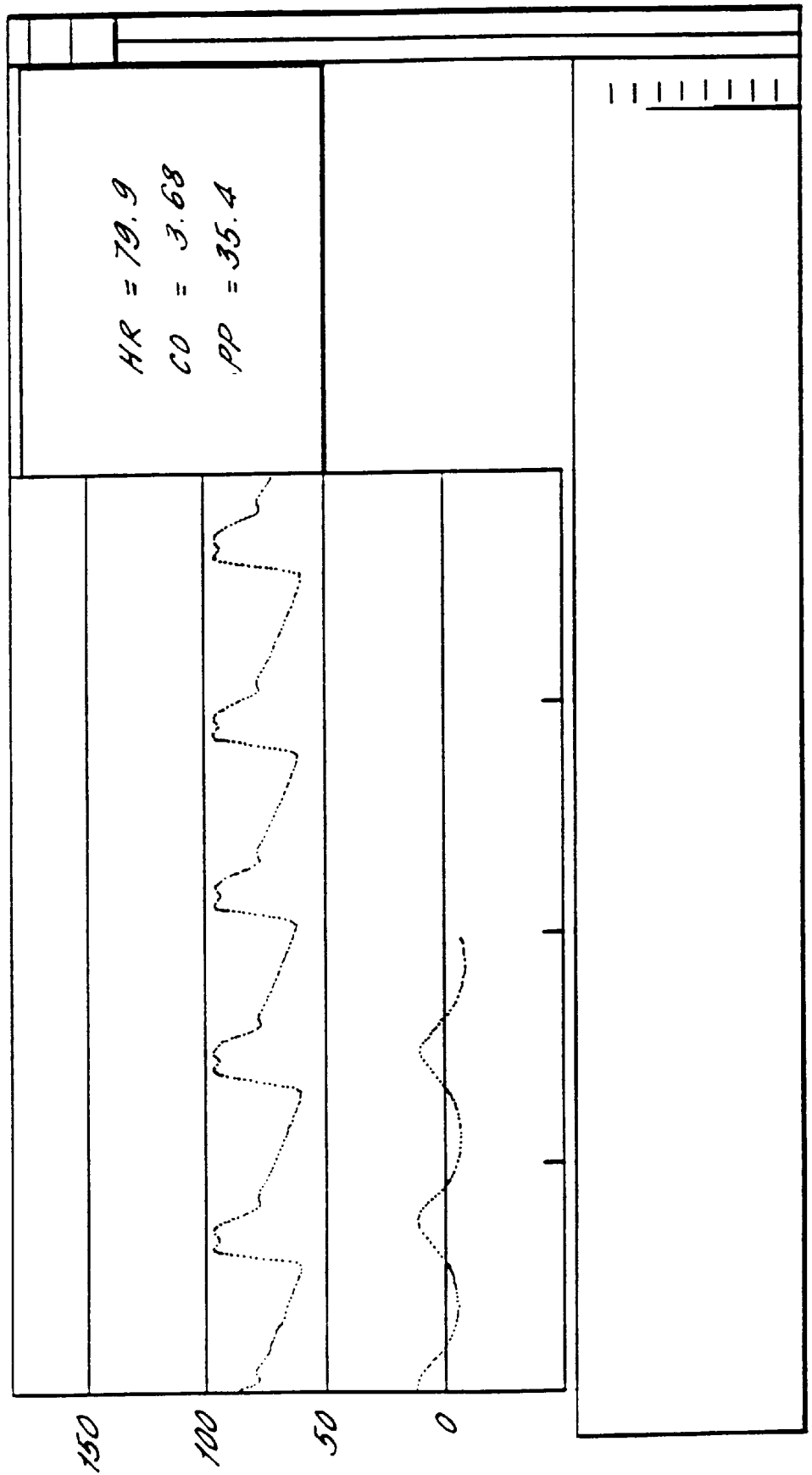

FIG. 2—The arterial wave form shows a secondary wave at the peak as well as a dicrotic notch on the descending limb. The heart rate again is 79.9 beats per minute. Both these patients were electrically paced at a nominal 80 bpm.

Figure 3:
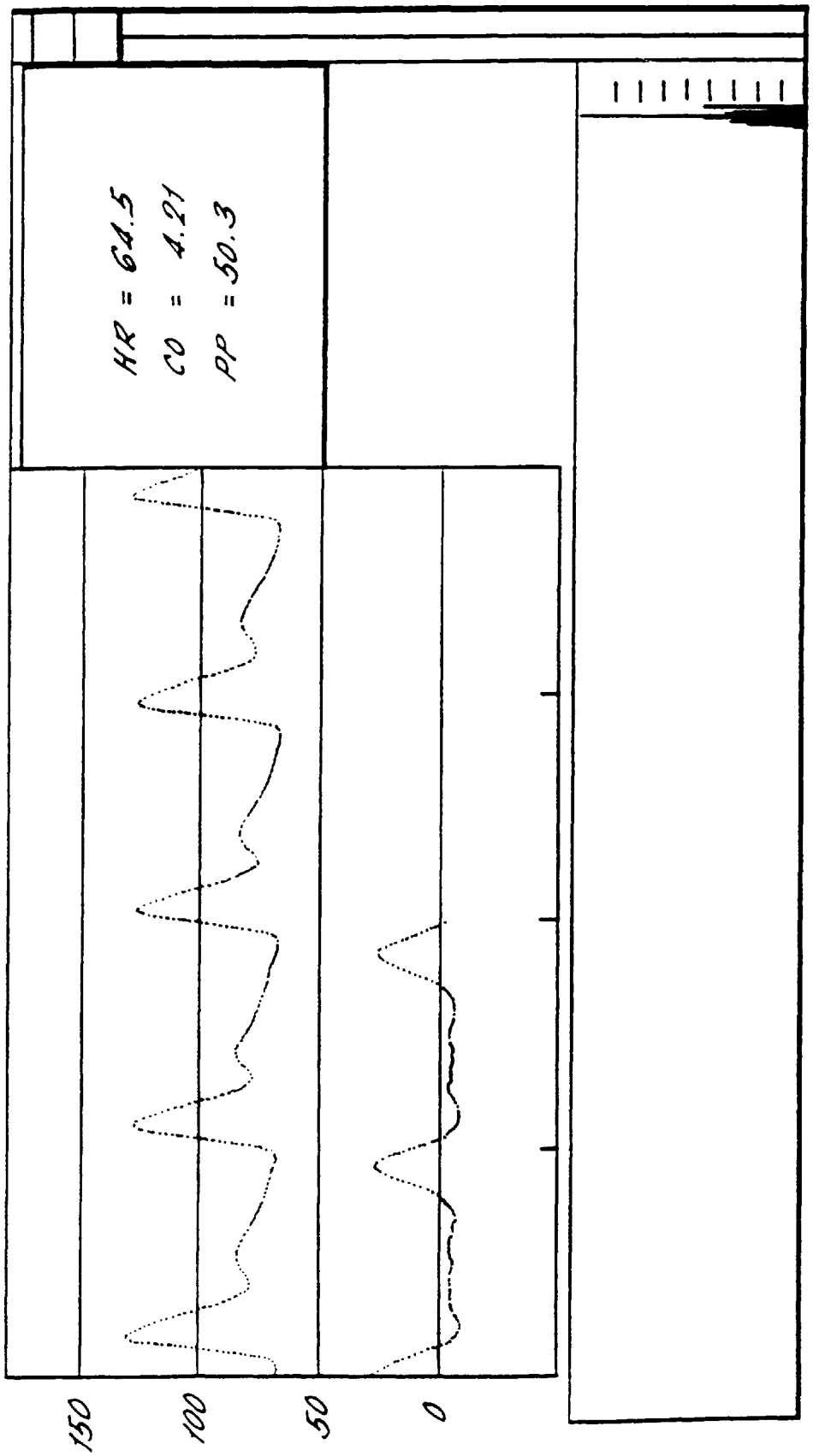

FIG. 3—This shows a pronounced and delayed diastolic wave. The autocorrelation gives the correct heart rate.

Figure 4:
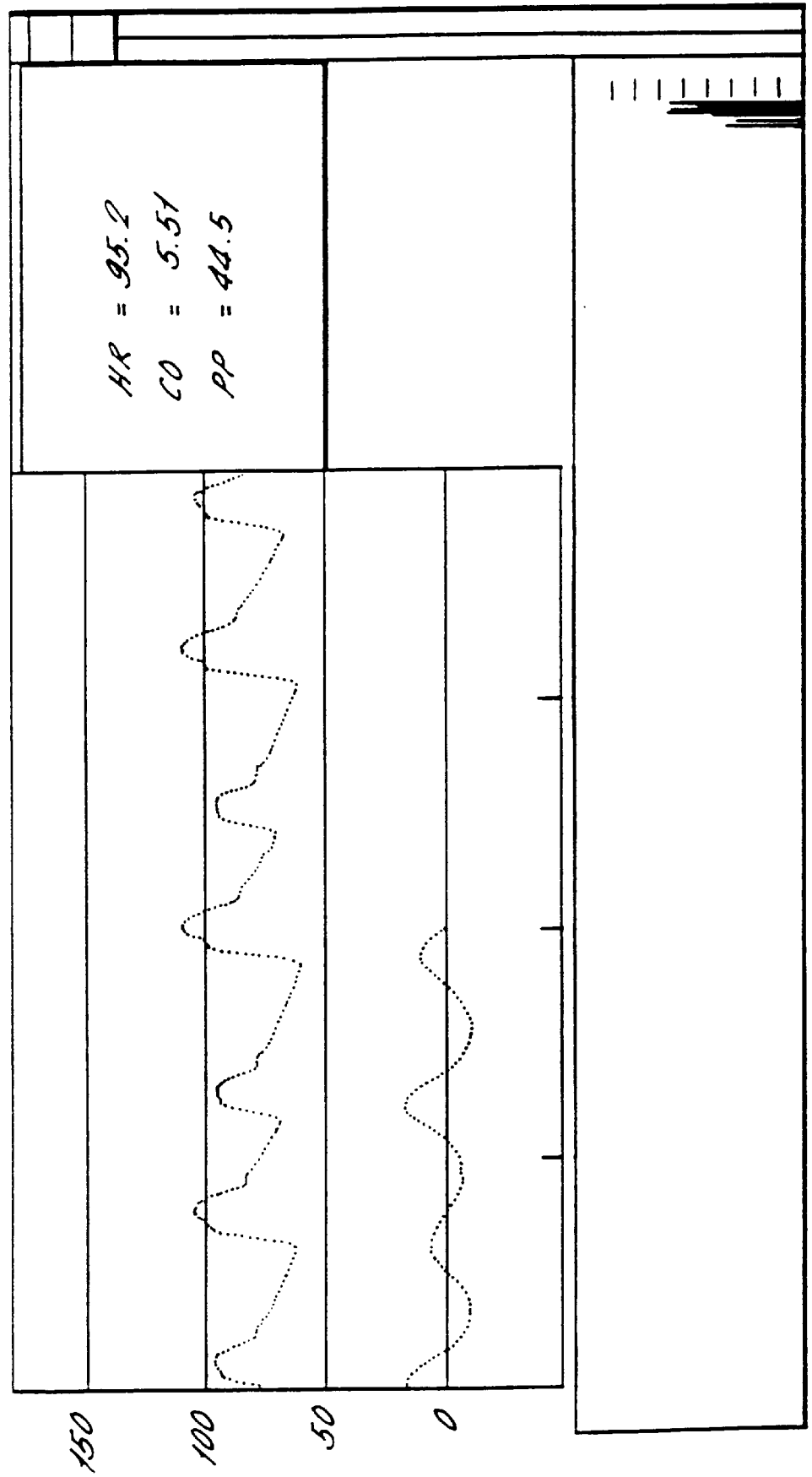

FIG. 4—This shows an alternating pattern in the heart beat. The autocorrelation estimates the rate correctly and shows that alternate beats correlate better than adjacent beats.

FIGS. 5a and 5b are graphs which compare cardiac output measurements obtained using the prior art lithium dilution method as disclosed in WO 93/09427 and the first method of the present invention. The close correlation of the results clearly indicates the merits of the present invention.

What is claimed is:

1. A method for the measurement of cardiac output in a patient, which method comprises:

(i) recording and storing the arterial blood pressure waveform of a patient from a blood pressure monitoring device over a period of time;

(ii) subjecting the waveform obtained in (i) to a non-linear transformation that corrects for the variation of the characteristics of the arterial system with pressure and thereby obtaining a corrected waveform;

(iii) subjecting the corrected waveform from (ii) to autocorrelation in order to derive the pulsatility which is equal to $$\sqrt{R(0)} + \sqrt{-R(\tau_{min})}$$

where $R(\tau)$ is the autocorrelation function and $\tau_{min}$ is the value of $\tau$ at which the autocorrelation is at a minimum and heart rate of the corrected waveform;

(iv) calculating the nominal stroke volume from the pulsatility;

(v) obtaining the nominal cardiac output by multiplying the nominal stroke volume by the heart rate; and (vi) obtaining the cardiac output from the nominal cardiac output by means of a calibration factor.

2. A method as claimed in claim 1 wherein the arterial blood pressure is recorded and stored in (i) for a period of up to ten seconds.

3. A method as claimed in claim 2 wherein the arterial blood pressure is recorded and stored in (i) for a period of up to four seconds.

4. A method as claimed in claim 1 wherein the non-linear transformation in step (ii) is effected using a look up table, with the mean of the data then being found and subtracted from each of the values obtained in (i).

5. A method as claimed in claim 1 wherein the nominal stroke volume is obtained by multiplying the pulsatility by a predetermined calibration factor.

6. A method as claimed in claim 5 wherein the predetermined calibration factor is obtained for a particular patient using a known calibration method.

7. A method as claimed in claim 6 wherein the calibration method is an indicator dilution method.

8. A method for the measurement of cardiac output in a patient, which method comprises:

(a) recording and storing the arterial blood pressure waveform of a patient from a blood pressure monitoring device over a period of time;

(b) obtaining and subtracting the mean of the blood pressure waveform from each of the values obtained in (a) and subjecting the data so obtained to autocorrelation;

(c) transforming the data from (b) into data which relates to the pulsatility which is equal to $$\sqrt{R(0)} + \sqrt{-R(\tau_{min})}$$

where $R(\tau)$ is the autocorrelation function and $\tau_{min}$ is the value of $\tau$ at which the autocorrelation is at a minimum and heart rate of the waveform;

(d) calculating the nominal stroke volume from the pulsatility;

(e) obtaining the nominal cardiac output by multiplying the nominal stroke volume by the heart rate; and (f) obtaining the cardiac output from the nominal cardiac output by means of a calibration factor.

9. A method as claimed in claim 8 wherein the arterial blood pressure is recorded and stored in (a) for a period of up to ten seconds.

10. A method as claimed in claim 9 wherein the arterial blood pressure is recorded and stored in (a) for a period of up to four seconds.

11. A method as claimed in claim 8 wherein the nominal stroke volume is obtained by multiplying the pulsatility by a predetermined calibration factor.

12. A method as claimed in claim 11 wherein the predetermined calibration factor is obtained for a particular patient using a known calibration method.

13. A method as claimed in claim 12 wherein the calibration method is an indicator dilution method.

14. Apparatus for the measurement of cardiac output in a patient, which comprises:

means for monitoring the arterial blood pressure of a patient;

means for monitoring the heart rate of a patient;

means for recording and storing the arterial blood pressure waveform of a patient;

means for transforming the blood pressure waveform to correct for the variation of the characteristics of the arterial system with pressure and thereby obtaining transformed data;

means for autocorrelating the transformed data and deriving the pulsatility which is equal to $$\sqrt{R(0)} + \sqrt{-R(\tau_{min})}$$

where $R(\tau)$ is the autocorrelation function and $\tau_{min}$ is the value of $\tau$ at which the autocorrelation is at a minimum and heart rate of the waveform therefrom;

means to calculate the nominal cardiac output from the measurements of heart rate of the patient and the pulsatility of the waveform; and means to converting the nominal cardiac output into the cardiac output.

15. Apparatus as claimed in claim 14 wherein the means for transforming the pressure waveform comprises a look up table.

16. Apparatus as claimed in claim 14 which includes means to calibrate the device.

17. Apparatus for the measurement of cardiac output in a patient, which comprises:

means for monitoring the arterial blood pressure of a patient;

means for monitoring the heart rate of a patient;

means for recording and storing the arterial blood pressure waveform of a patient;

means for obtaining and subtracting the mean of the blood pressure waveform from each of the values of the blood pressure and means for subjecting the data so obtained to autocorrelation;

means for transforming the autocorrelated data into data relating to the pulsatility which is equal to $$\sqrt{R(0)} + \sqrt{-R(\tau_{min})}$$

where $R(\tau)$ is the autocorrelation function and $\tau_{min}$ is the value of $\tau$ at which the autocorrelation is at a minimum and heart rate of the blood pressure waveform;

means to calculate the nominal cardiac output from the measurements of heart rate of the patient and the pulsatility of the waveform; and means for converting the nominal cardiac output into the cardiac output.

* * * * *